US009284267B2

(12) United States Patent
Jacob et al.

(10) Patent No.: US 9,284,267 B2

(45) Date of Patent: Mar. 15, 2016

(54) PROCESS FOR THE PREPARATION OF URETHANES

(75) Inventors: Andreas Jacob, Marburg (DE); Stefan Wershofen, Mönchengladbach (DE); Stephan Klein, Mettmann (DE); Jörg Sundermeyer, Marburg (DE); Fuming Mei, Hubei (CN)

(73) Assignee: Bayer MaterialScience AG, Leverkusen (DE)

( * ) Notice: Subject to any disclaimer, the term of this patent is extended or adjusted under 35 U.S.C. 154(b) by 454 days.

(21) Appl. No.: 12/321,995

(22) Filed: Jan. 28, 2009

(65) Prior Publication Data

US 2009/0275771 A1 Nov. 5, 2009

(30) Foreign Application Priority Data

Jan. 31, 2008 (DE) ......................... 10 2008 006 881

(51) Int. Cl.

*C07C 263/04* (2006.01)
*C07C 269/04* (2006.01)
*C07C 273/18* (2006.01)

(52) U.S. Cl.

CPC ............. *C07C 263/04* (2013.01); *C07C 269/04* (2013.01); *C07C 273/18* (2013.01)

(58) Field of Classification Search

None

See application file for complete search history.

(56) References Cited

U.S. PATENT DOCUMENTS

| | | | | |
|---|---|---|---|---|
| 3,481,967 | A | 12/1969 | Ottmann et al. | |
| 4,266,077 | A | 5/1981 | Conrow et al. | |
| 4,705,883 | A * | 11/1987 | Grate et al. | 560/25 |
| 5,194,660 | A | 3/1993 | Leung et al. | |
| 2002/0001977 | A1 * | 1/2002 | Gole et al. | 438/800 |
| 2005/0167337 | A1 * | 8/2005 | Bunger et al. | 208/254 R |
| 2007/0293696 | A1 | 12/2007 | Serrano Fernandez et al. | |

FOREIGN PATENT DOCUMENTS

| | | | |
|---|---|---|---|
| EP | 1870397 | A1 | 12/2007 |
| WO | 2006131381 | A1 | 12/2006 |

OTHER PUBLICATIONS

Nefedov, B.K. et al, Selective Synthesis of Chlorine-Substituted Phenyl Isocyanates by Catalytic Carbonylation of Chloronitrobenzenes with Carbon Monoxide, Chem. Proc. Acad. Sci, USSR, vol. 234, pp. 347-350, (1977).

Benedini, Francesca et al, The Bis(Salicylaldehyde)Ethylenediimine Cobalt(II)-Catalysed Oxidative Carbonylation of Primary and Secondary Amines, Journal of Molecular Catalysis, 34 (1986), pp. 155-161, Elsevier Sequoia, The Netherlands.

Maddinelli, Giuseppe et al, The Bis-(Salicylaldehyde)Ethylenediimine Cobalt(II)-Catalysed Oxidative Carbonylation of 1-Adamantylamine in Alcohol: A Study for Optimising Carbamate Formation, Journal of Molecular Catalysis, 39 (1987), pp. 71-77, Elsevier Sequoia, The Netherlands.

Orejon, Aranzazu et al, Oxidative Carbonylation of Aniline with New Cobalt Catalytic Systems, Can. J. Chem. 83 (2005), pp. 764-768, NRC Canada.

Leigh, G.J., Nomenclature of Inorganic Chemistry (1990), p. 282, Blackwell Scientific Publications.

Bolzacchini, Ezio et al, “Substituent effects in the cobalt-catalyzed oxidative carbonylation of aromatic amines”, Journal of Molecular Catalysis A: Chemical, 111 (1996), pp. 281-287.

Bassoli, Angela et al, “Metal carbonyl catalyzed reductive carbonylation of substituted nitrobenzenes in presence of alkenes as solvents”, Journal of Molecular Catalysis, 60, (1990), pp. 155-163.

* cited by examiner

*Primary Examiner* — Sudhakar Katakam

*Assistant Examiner* — Jennifer C Sawyer

(74) *Attorney, Agent, or Firm* — Donald R. Palladino; Lyndanne M. Whalen

(57) ABSTRACT

Urethanes are prepared by oxidative carbonylation of at least one amino compound in the presence of carbon monoxide, oxygen and organic, at least one hydroxyl-group-carrying compound. The carbonylation is carried out in the absence of halogen-containing promoters. The carbonylation is also carried out in the presence of a metal complex catalyst which contains neutral bidentate N-chelate ligands of the (N~N) type, two monoanionic N,O-chelate ligands of the general type $(N{\sim}O)^-$ or tetradentate dianionic chelate ligands $(O{\sim}N{\sim}N{\sim}O)^{2-}$.

7 Claims, No Drawings

PROCESS FOR THE PREPARATION OF URETHANES

BACKGROUND OF THE INVENTION

The invention relates to a process for the preparation of urethanes and/or ureas by oxidative carbonylation of amino compounds in the presence of carbon monoxide and oxygen as oxidizing agents and, particularly in the case of the urethanes, in the presence of an organic compound containing one or more hydroxyl groups.

The preparation of isocyanates, urethanes (which are also referred to as carbamates) and also ureas on an industrial scale currently includes the reaction of the corresponding primary amine with phosgene. Large amounts of hydrogen chloride are formed as a by-product of this reaction and must be disposed of or used further in coupled processes in a relatively expensive manner. There is therefore a great interest, on the part of industry, in developing non-coupled synthesis processes which can be carried out without the use of phosgene and which avoid the by-product hydrogen chloride.

Ottmann et al. (U.S. Pat. No. 3,481,967) describes a process for the preparation of aromatic isocyanates in which aromatic nitro compounds and carbon monoxide can be prepared in the presence of transition metal catalysts. These transition metal catalysts include cobalt iodide and titanium tetrachloride. However, industrially useful processes must have a high conversion and a selectivity of over 90%, where possible, in order to be used successfully. To date, only reductive carbonylation processes have been able to meet these requirements. Such reductive carbonylation processes start with aromatic nitro compounds and use expensive noble metal catalysts (B. K. Nefedov, V. I. Manov-Yuvenskii, S. S. Novikov, Doklady (Chem. Proc. Acad. Sci. USSR), 234, 347 (1977)). In most cases, it is difficult to recover the noble metal catalysts. Therefore, these processes are not acceptable from an economic point of view. One exception is patent WO 2006 131 381 A1, which teaches oxidation of aromatic amines with corresponding aromatic nitro compounds as the oxidizing agent, in the presence of alcohols and acidic promoters, in order to obtain urethanes. Unlike oxygen, however, nitro compounds are comparatively expensive oxidizing agents which must be prepared in a separate process. Both constitute disadvantages.

Industrial and scientific research has therefore concentrated predominantly on the development of processes in which aromatic nitro compounds are converted into N-arylurethanes in the presence of carbon monoxide and an organic, hydroxyl-group-containing compound by oxidative carbonylation in the presence of oxygen. The N-arylurethanes can be converted into the corresponding N-aryl isocyanates in a further process step. An example of this type of process is disclosed in U.S. Pat. No. 4,266,077, in which aromatic amines are reacted in the presence of $Co_2(CO)_8$ as catalyst, an organic hydroxyl-group-containing compound and an unsaturated organic component. The latter is necessary to ensure high selectivities. In addition, it is expressly stated that no oxidizing agent, such as oxygen, is used.

Benedini et al. was the first to use [$Co^{II}$(salen)] (salen=N,N'-disalicylidene-ethylenediamine) as catalyst in order to convert aromatic or aliphatic primary amines into the corresponding urethanes or ureas in the presence of methanol (F. Benedini, M. Nali, B. Rindone, S. Tollari, J. Mol. Catal, 1986, 34, 155-161; G. Maddinelli, M. Nali, B. Rindone, S. Tollari, J. Mol. Catal, 1987, 39, 71-77). Disadvantages of this process include the especially long reaction times of up to 48 hours and immensely high catalyst concentrations (up to 20 mol %).

The selectivities are moderate to good and a product mixture of the corresponding urethanes and ureas is generally obtained.

U.S. Pat. No. 5,194,660 describes the oxidative carbonylation of aromatic amines in the presence of carbon monoxide and an organic hydroxyl-group-containing compound and also oxygen as oxidizing agent. Macrocyclic transition metal complex catalysts are used. One of the disadvantages of this process is its use of large amounts of lithium iodide as promoter. The process is not conducted halogen-free, and corrosion problems which can scarcely be overcome are further disadvantages.

Orejon et al. further developed the work of Benedini et al. using hydrolytically stable ligands based on 2,2'-bipyridine or 1,10-phenanthroline. In comparison with the salen ligand, these ligands lack the hydrolytically sensitive imine unit. However, in this work, express reference is also made to the use of alkali halide promoters (A. Orejon, A. Castellanos, P. Salagre, S. Castillón, C. Clayer, J. Can. Chem., 2005, 83, 764-768).

A similar process is described in published patent application U.S. 2007/0293696 A1. In U.S. 2007/0293696, however, the use of a halogen-containing compound as solvent is an essential part of the process. A disadvantage is that the halogen-containing compounds used as solvents are considered harmful from an environmental point of view.

SUMMARY OF THE INVENTION

The object of the present invention was, therefore, to develop a process for the production of urethanes and/or ureas which does not require halogen-containing promoters in which the corresponding primary amines are reacted by oxidative carbonylation in the presence of oxygen with high conversions and selectivities.

This and other objects which will be apparent to those skilled in the art has been achieved by using metal complex catalysts containing a ligand selected from a specified group in the oxidative carbonylation reaction.

DETAILED DESCRIPTION OF THE INVENTION

It has now been found that a process for the preparation of urethanes and/or ureas by oxidative carbonylation of the corresponding organic amino compounds in the presence of carbon monoxide, oxygen and organic, hydroxyl-group-carrying compounds leads to excellent results when the carbonylation is carried out without the use of halogen-containing promoters in the presence of metal complex catalysts which contain neutral bidentate N-chelate ligands of the (N~N) type, two monoanionic N,O-chelate ligands of the general type $(N{\sim}O)^-$ or tetradentate dianionic chelate ligands $(O{\sim}N{\sim}N{\sim}O)^{2-}$. The metal complex catalysts accordingly correspond to the general types [M(N~N)], $[M(N{\sim}O)_2]$ or [M(O~N~N~O)], wherein M represents a di- or tri-valent transition metal of groups 5 to 11 (G. J. Leigh, Nomenclature of Inorganic Chemistry, Blackwell Scientific Publications, London, 1990, p. 282).

The present invention relates to a process for the preparation of urethanes by oxidative carbonylation of amino compounds in the presence of carbon monoxide, oxygen and organic, hydroxyl-group-carrying compounds. In this process, the carbonylation is carried out in the absence of halogen-containing promoters and in the presence of metal complex catalysts which contain neutral bidentate N-chelate ligands of the (N~N) type, two monoanionic N,O-chelate ligands of the general type (N~O)⁻ or tetradentate dianionic chelate ligands $(O{\sim}N{\sim}N{\sim}O)^{2-}$.

Within the scope of this invention, the expression "absence of halogen-containing promoters in the carbonylation" means a maximum content of halogen-containing promoters of less than 0.04 wt. %, preferably of less than 0.03 wt. %, most preferably of from 0.001 to 0.02 wt. %, based on the weight of the reaction mixture. The preferred range of from 0.001 to 0.02 wt. % halogen-containing promoters is derived from the fact that very small amounts of halogen-containing promoter scarcely interfere with the process according to the invention, but the removal of such halogen-containing promoter (which may be necessary even if only trace amounts are present) before the carbonylation process is carried out represents a disproportionately high expenditure.

Within the scope of the present invention, "promoters" are substances which are neither a catalyst nor a catalyst precursor or any decomposition product of the catalyst.

It has been found that the pre-catalyst complexes mentioned in the schemes below preferably achieve the above-mentioned object without the addition of halogen-containing promoters:

Formula scheme I:

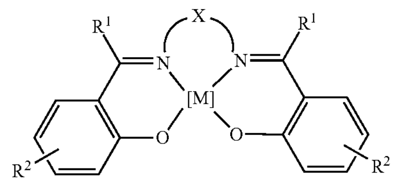

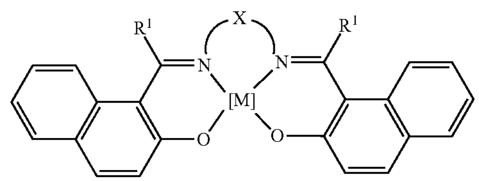

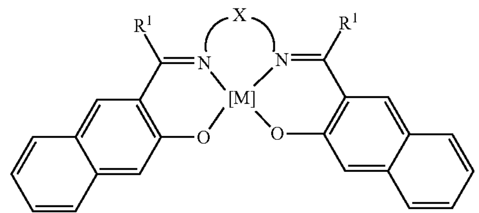

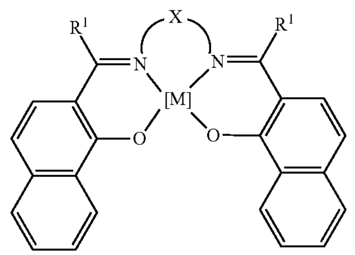

-continued

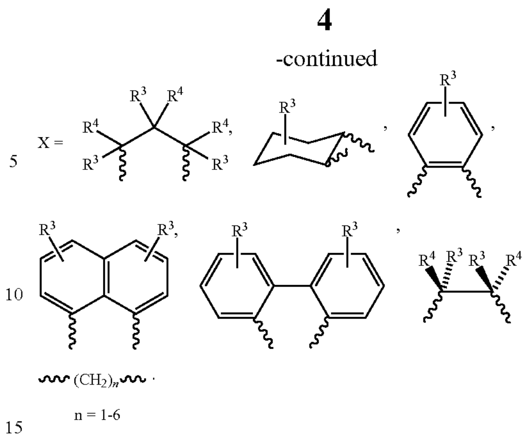

M is a di- or tri-valent metal of groups 5 to 11 of the Periodic System of the Elements.

Suitable metals M for the metal complex catalysts include: vanadium, chromium, manganese, iron, cobalt, nickel, copper, zirconium, niobium, molybdenum, ruthenium, rhodium, palladium, silver, hafnium, tantalum, tungsten, rhenium, osmium, iridium, platinum, and gold. Preferred metals include cobalt, manganese, chromium, nickel, copper, as well as some 4d metals, such as rhodium and ruthenium, and 5d metals, such as iridium and platinum. Cobalt is most preferred.

Within the scope of this invention, the term "4d metal" means a transition metal of the 4th Period of the Periodic System of the Elements. The same principle applies to references made to other metals such as the "5d" metals (i.e., those metals in the 5th Period of the Periodic System).

The designation [M] includes the supplementation of the coordination sphere of the metal with up to two additional ligands L, in addition to the ligand type claimed here, to form an octahedric environment. This means that [M] represents a place holder for a di- or tri-valent transition metal of coordination number 4 or of coordination number 5 [M]=L–M or of coordination number 6 [M]=L–M–L.

These additional ligands L can be either neutral ligands, for example solvent molecules, or monoanionic ligands. The most preferred ligands L are $H_2O$, $R_nNH_{3-n}$, halide, carboxylate (e.g. benzoate, acetate, trifluoroacetate, formate), sulfonate (e.g. triflate, tosylate), pseudohalide (e.g., CN, SCN, OCN, $N_3$), an aza-aromatic compound, a cyclic or acyclic amine or ketimine $R_2C{=}NR$; an aliphatic ether or an aliphatic or aromatic alcohol. R and R' here represent an aryl or alkyl group having from 1 to 20 carbon atoms, an O-alkyl, NH(alkyl) or $N(alkyl)_2$ group. The ligands L can also be absent in the catalyst precursor isolated as substance. In solution, the ligands L can be solvent molecules, which can readily be substituted by the reacted substrates.

$R^1$ represents hydrogen, an alkyl radical having from 1 to 20 carbon atoms, an aryl or heteroaryl group, an OR group in which R represents hydrogen or an alkyl group having from 1 to 20 carbon atoms, or a NRR' group in which R and R' represent hydrogen or, independently of one another, an aryl or alkyl group having from 1 to 20 carbon atoms, or R and R' together can form a ring system containing a nitrogen atom as heteroatom.

$R^2$ represents hydrogen, an alkyl group having from 1 to 20 carbon atoms, an aryl group or heteroaryl group which is linked via a bond to the salicylate structural unit or is fused via two C—C bonds, a keto group —COR, also —COOR, —COOH, fluorine, chlorine, bromine, iodine, OH, OR or NRR', wherein R and R' can have the meanings given above, and $R^2$ can substitute the aromatic ring from 1 to 4 times.

$R^3$ and $R^4$ can be hydrogen, an alkyl group having from 1 to 20 carbon atoms, an aryl or heteroaryl group, a keto group —COR, also —COOR, —COOH, fluorine, chlorine, bromine, iodine, OH, OR or NRR', wherein R and R' can have the meanings given above.

X according to formula scheme I is any of the mentioned alkylene or arylene structural units which links the two imino nitrogen atoms with one another. This unit X can also be linked via its central substituent $R^3$ or $R^4$ to further molecular, macromolecular or inorganic structural elements.

The highly active catalyst complexes of the salen type (Formula A), in which $R^1$ represents H, methyl (Me) or phenyl (Ph) is preferred.

Formula A

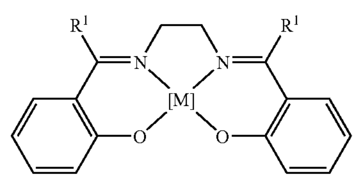

Also preferred is the salophen type (formula B), in which $R^1$ represents H, methyl (Me) or phenyl (Ph).

Formula B

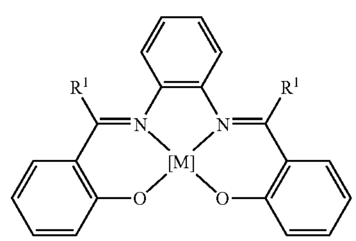

Catalysts which can be used in the process of the present invention also include metal complex compounds having other dianionic $N_2O_2$-chelate ligands which combine carboxylate, aza-aromatic, phenolate and/or metallized carboxylic acid amide functions. Suitable ligands having particularly preferred structural elements are described more precisely in Formula scheme II and Formula scheme III below:

Formula scheme II

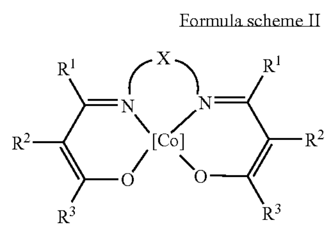

-continued

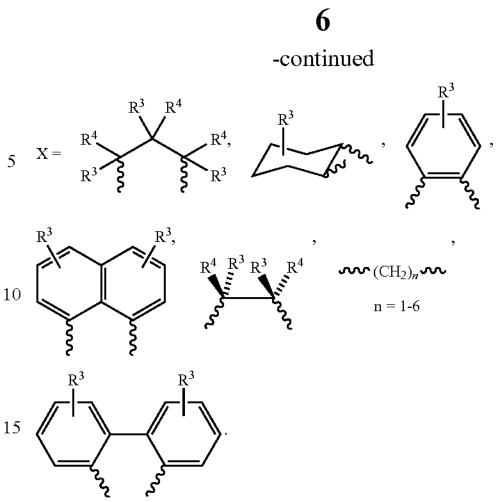

In formula scheme II, $R^1$, $R^2$, $R^3$, $R^4$, [X] and [M] are as defined in Formula scheme I.

Formula scheme III

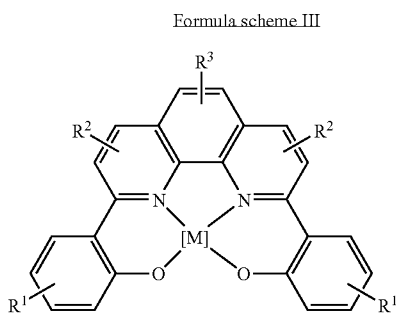

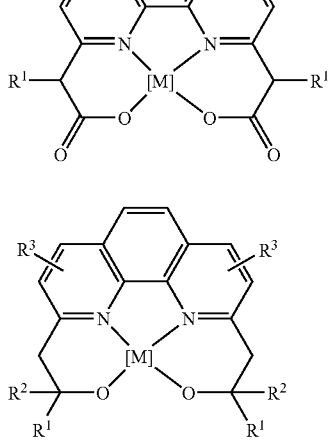

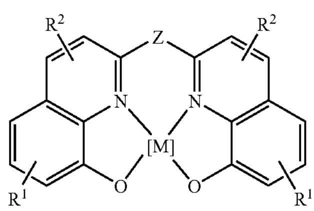

-continued
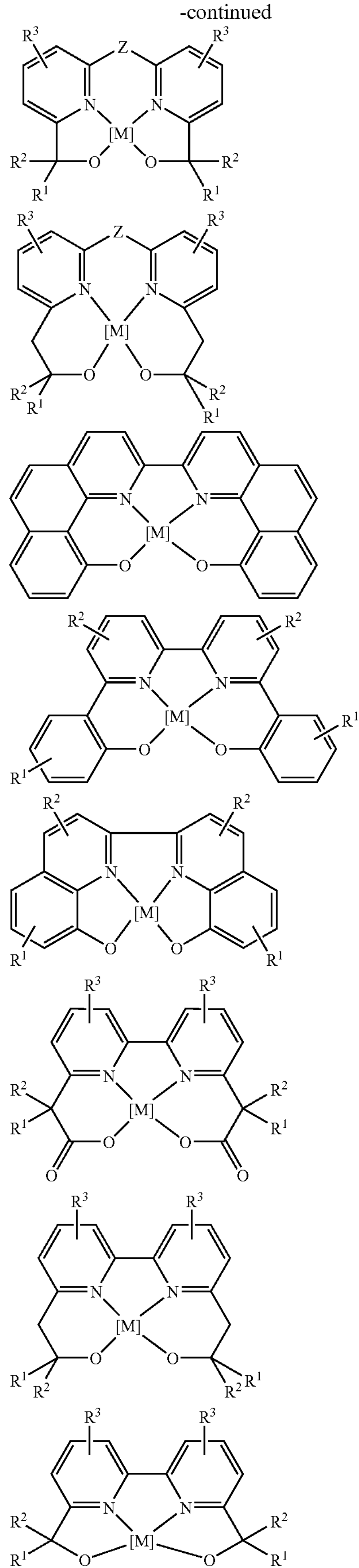
-continued
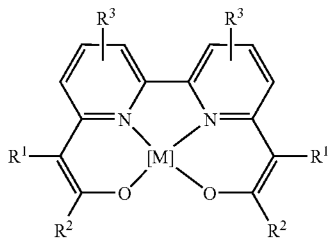
In formula scheme III, Z represents NH, N-alkyl, N-aryl, O, S, CO, $CH_2$, or CHR where R=$C_1$-$C_{20}$-alkyl, $CR_2$ or -aryl group(s).
Suitable alternative catalysts to the dianionic $N_2O_2$ ligand, are two monoanionic, at least bidentate N,O-chelate ligands.
Formula scheme IV
IV
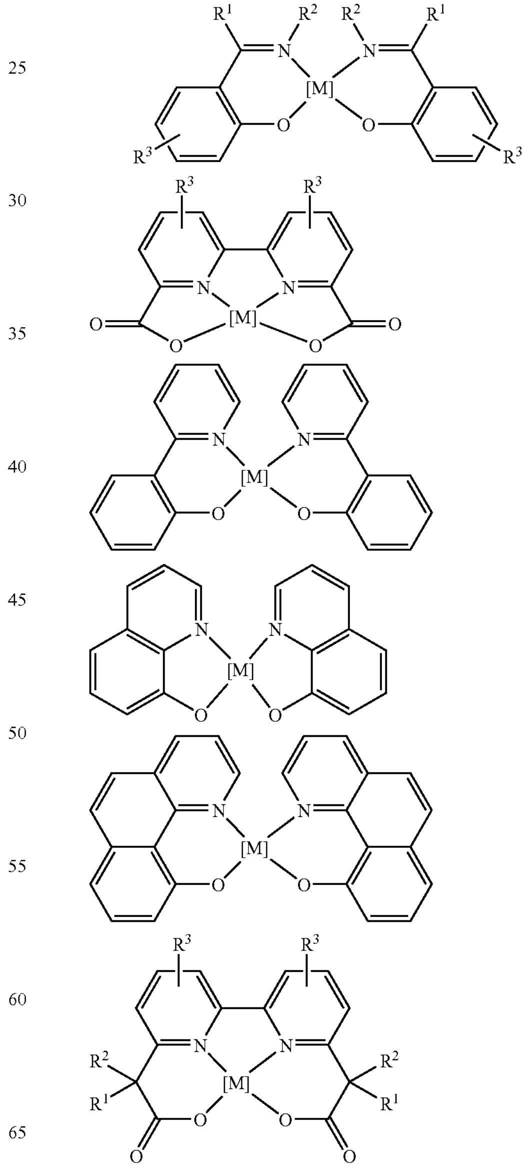

-continued

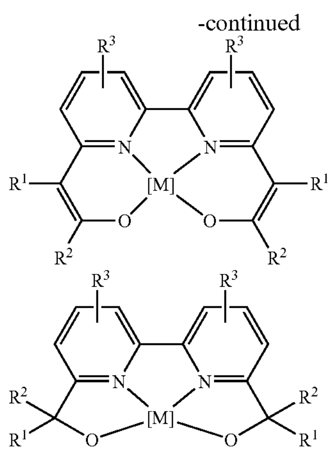

In each of Formula schemes III and IV, the substituents have the following meanings:

$R^1$ represents hydrogen, an alkyl radical having from 1 to 20 carbon atoms, an aryl or heteroaryl group, an OR group in which R represents hydrogen or an alkyl group having from 1 to 20 carbon atoms, or an NRR' group in which R and R' each represent hydrogen or, independently of one another, an aryl or alkyl group having from 1 to 20 carbon atoms, or R and R' together form a ring system having a nitrogen atom as heteroatom.

$R^2$ represents hydrogen, an alkyl group having from 1 to 20 carbon atoms, an aryl group or heteroaryl group which is linked via a bond to the salicylate structural unit or is fused via two C—C bonds, a keto group —COR, also —COOR, —COOH, fluorine, chlorine, bromine, iodine, OH, OR or NRR', wherein R and R' can have the meanings given above, and $R^2$ can substitute the aromatic ring from 1 to 4 times.

$R^3$ and $R^4$ each represent hydrogen, an alkyl group having from 1 to 20 carbon atoms, an aryl or heteroaryl group, a keto group —COR, also —COOR, —COOH, fluorine, chlorine, bromine, iodine, OH, OR or NRR', wherein R and R' can have the meanings given above.

X represents any of the mentioned alkylene or arylene structural units which links the two imino nitrogen atoms with one another. X can also be linked via its central substituent $R^3$ or $R^4$ with further molecular, macromolecular or inorganic structural elements.

The designation [M] includes the supplementation of the coordination sphere of the metal by up to two further ligands L, in addition to the ligand type described here, to form an octahedric environment. This means that [M] represents a place holder for a di- or tri-valent transition metal of coordination number 4 or of coordination number 5: [M]=L–M or of coordination number 6: [M]=L–M–L.

These additional ligands L can be either neutral ligands, for example solvent molecules, or monoanionic ligands. Preferred ligands include $H_2O$, $R_nNH_{3-n}$, halide, carboxylate (e.g., benzoate, acetate, trifluoroacetate, formate), sulfonate (e.g. triflate, tosylate), $BF_4^-$, $PF_6^-$, $SbF_6^-$, pseudohalide (e.g., CN, SCN, OCN, $N_3$), an aza-aromatic compound, a cyclic or acyclic amine or ketimine $R_2C{=}NR$; an aliphatic ether or an aliphatic or aromatic alcohol. R and R' here represent an aryl or alkyl group having from 1 to 20 carbon atoms, an —O-alkyl, NH(alkyl) or —N(alkyl)$_2$ group. The ligands L can also be absent in the isolated catalyst precursor. In solution, the ligands L can be solvent molecules, which can readily be substituted by the reacted substrates.

The process of the present invention is based on Schiff's base complexes known in principle in the literature. Complexes of the inexpensive 3d metal cobalt have particularly high activity. Complexes of the cobalt-salen and cobalt-salophen type (Formulae A and B) have been found to be particularly suitable as catalysts. Their common structural element is two salicylidene-amino structural groups linked by a diamino spacer X. These catalysts have the following general lead structure (Formula scheme V) (C. Srivanavit, D. G. Brown, J. Am. Chem. Soc., 1978, 100, 5777-5783; H. Aoi, M. Ishihiro, S. Yoshikawa, T. Tsuruta, J. Org. Chem., 1975, 85, 241-248; M. R. Mahmoud, S. A. Ibrahim, N. M. Ismail, Monatshefte für Chemie, 1985, 116, 167-175; C. Fukuhara, E. Asato, T. Shimoji, K. Katsura, J. Chem. Soc., Dalton Trans., 1987, 1305-1311; K. Maruyama, T. Kusukawa, Y. Higuchi, A. Nishinaga, Chemistry Letters, 1991, 7, 1093-1096):

Formula scheme V

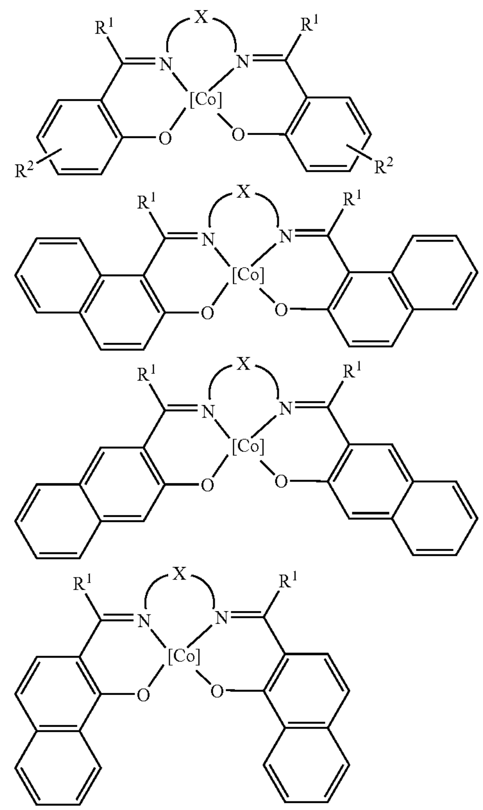

In Formula scheme V, [Co] represents cobalt in its di- or tri-valent oxidation state. The designation [Co] also includes the supplementation of the coordination sphere of the metal by up to two further ligands L, in addition to the ligand type mentioned here, to form an octahedric environment. This means that [Co] represents a space holder for a di- or tri-valent cobalt of coordination number 4 or coordination number 5: [Co]=L-Co or of coordination number 6: [Co]=L-Co-L.

These additional ligands L can be either neutral ligands, for example solvent molecules, or monoanionic ligands; $H_2O$, $R_nNH_{3-n}$, halide, carboxylate (e.g. benzoate, acetate, trifluoroacetate, formate), sulfonate (e.g. triflate, tosylate), pseudohalide (e.g., CN, SCN, OCN, $N_3$), an aza-aromatic compound, a cyclic or acyclic amine or ketimine $R_2C{=}NR$;

an aliphatic ether or an aliphatic or aromatic alcohol. R and R' here represent an aryl or alkyl group having from 1 to 20 carbon atoms, an —O-alkyl, NH(alkyl) or —N(alkyl)$_2$ group are preferred ligands. The ligands L can also be absent in the isolated catalyst precursor. In solution, the ligands L can be solvent molecules, which can readily be substituted by the reacted substrates.

$R^1$ represents hydrogen, an alkyl radical having from 1 to 20 carbon atoms, an aryl or heteroaryl group, an OR group in which R represents hydrogen or an alkyl group having from 1 to 20 carbon atoms, or NRR' in which R and R' each represent hydrogen or each represent an aryl or alkyl group having from 1 to 20 carbon atoms, or R and R' together can form a ring system containing a nitrogen atom as heteroatom.

$R^2$ represents hydrogen, an alkyl group having from 1 to 20 carbon atoms, an aryl group or heteroaryl group which is linked via one or two C—C bonds fused to the salicylate structural unit, a keto group —COR or —COOR, —COOH, fluorine, chlorine, bromine, iodine, OH, OR or NRR', wherein R and R' can have the meanings given above, and $R^2$ can substitute the aromatic ring from 1 to 4 times.

$R^3$ and $R^4$ each represent hydrogen, an alkyl group having from 1 to 20 carbon atoms, an aryl or heteroaryl group, a keto group —COR, also —COOR, —COOH, fluorine, chlorine, bromine, iodine, OH, OR or NRR', wherein R and R' can have the meanings given above.

X represents any of the alkylene or arylene structural units, already mentioned several times, which links the two imino nitrogen atoms with one another. This unit X can also be linked via its central substituents $R^3$ or $R^4$ to further molecular, macromolecular or inorganic structural elements.

Particular preference is given to the highly active catalyst complexes of the salen type (Formula A) in which $R^1$ represents H, methyl (Me) or phenyl (Ph), and Formula A

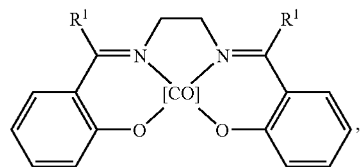

[Co] represents cobalt in its di- or tri-valent oxidation state.

Particular preference is given also to the salophen type (Formula B) in which $R^1$ represents H, methyl (Me) or phenyl (Ph), and Formula B

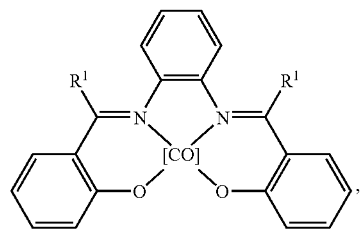

[Co] represents cobalt in its di- or tri-valent oxidation state.

Catalysts used in the process of the present invention are also metal complex compounds having other dianionic N$_2$O-chelate ligands, which combine carboxylate, aza-aromatic, phenolate and/or metallized carboxylic acid amide functions. Suitable ligands having particularly preferred structural elements are described more precisely as cobalt complexes in the following Formula scheme VI and Formula scheme VII:

Formula scheme VI

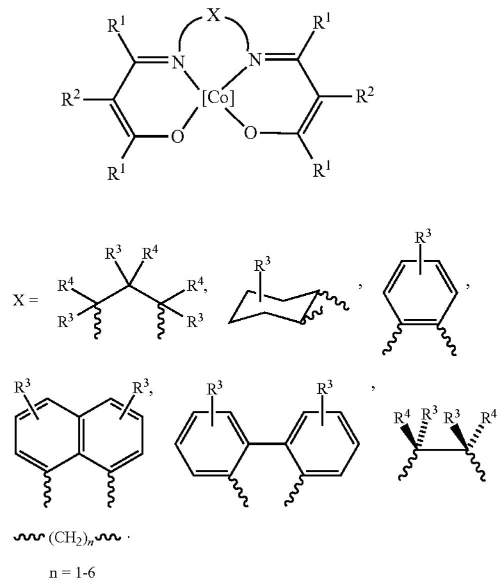

Formula scheme VII

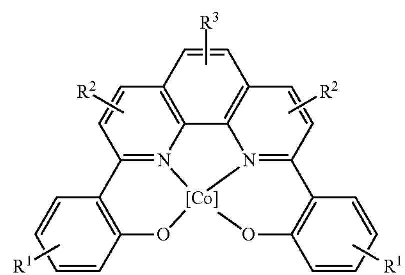

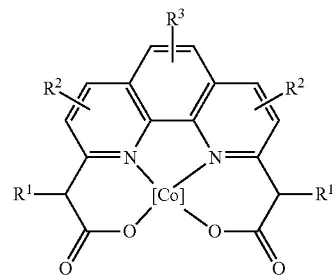

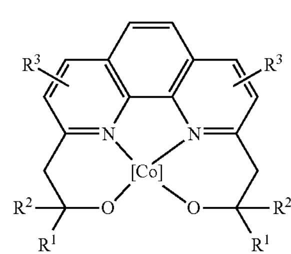

-continued
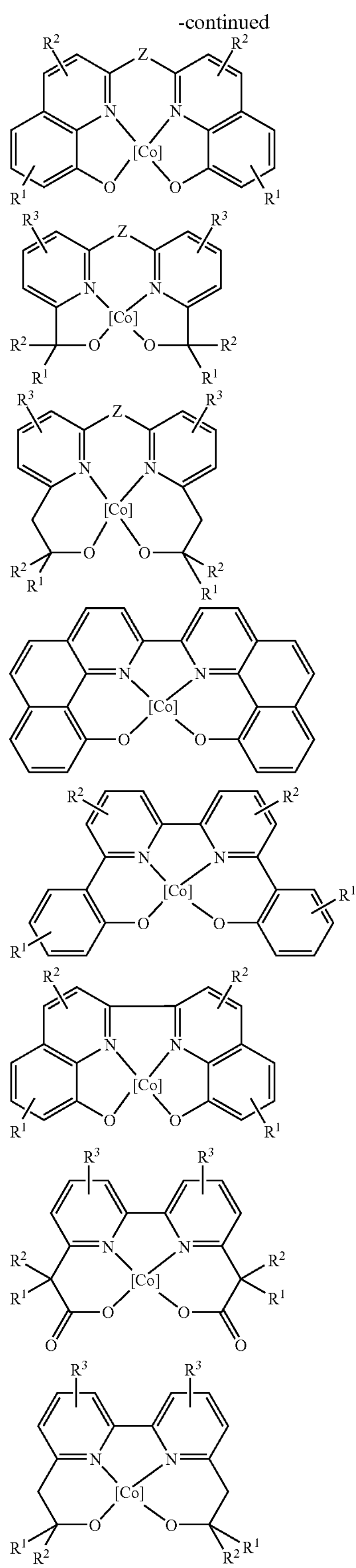
-continued
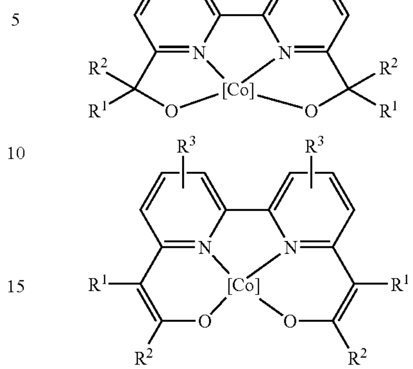
In Formula scheme VII, Z represents NH, N-alkyl, N-aryl, O, S, CO, $CH_2$, CHR where R=$C_1$-$C_{20}$-alkyl, $CR_2$ or -aryl.
Alternative catalysts to those having a dianionic $N_2O_2$ ligand are those having two monoanionic bidentate N,O-chelate ligands (Formula scheme VIII).
Formula scheme VIII
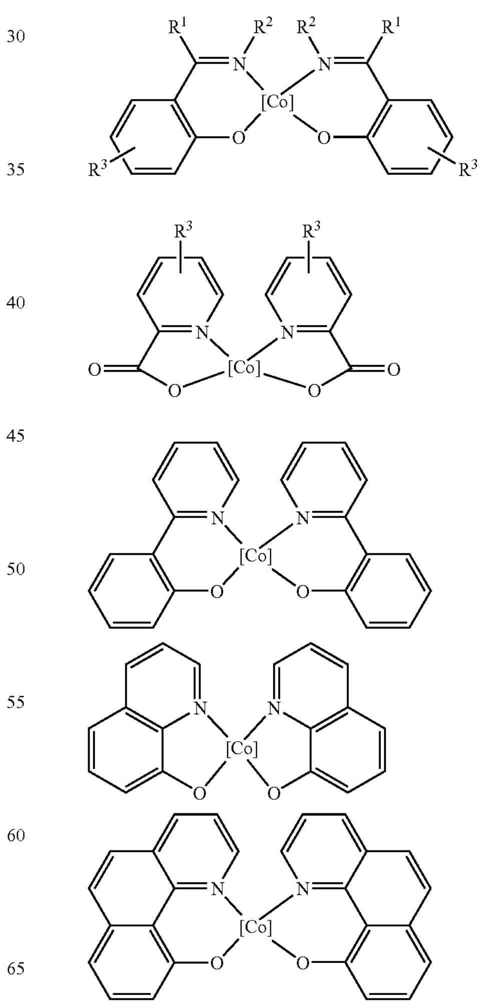

-continued

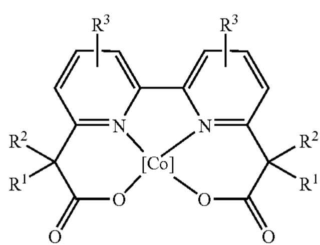

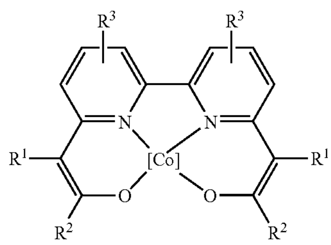

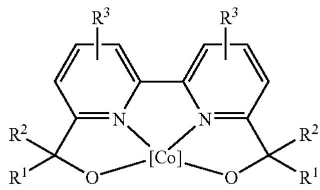

As an alternative to the structures shown in Formula schemes V to VIII, catalytically active complexes of di- and tri-valent cobalt salts $[Co]A_2$ and $[Co]A_3$ neutral N~N chelate ligands have proven successful. Proven N~N ligands are shown by way of example in Formula scheme IX.

Formula scheme IX

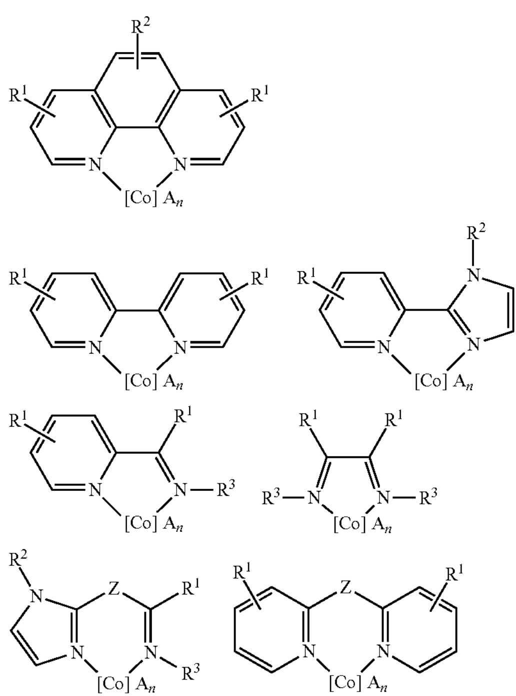

-continued

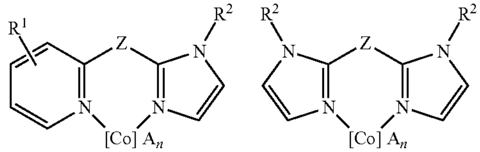

In Formula scheme IX, Z represents NH, N-alkyl, N-aryl, O, S, CO, $CH_2$, CHR where R=$C_1$-$C_{20}$-alkyl, $CR_2$ or -aryl. [Co] represents cobalt in its di- or tri-valent oxidation state.

In Formula scheme IX, A represents any desired anion in which n=2 or 3. The monovalent anions A can be, for example, independently of one another: halide, carboxylate (e.g., benzoate, acetate, trifluoroacetate, formate), sulfonate (e.g., triflate, tosylate), pseudohalide (e.g., CN, SCN, OCN, $N_3$), fluoro acid anions (e.g., $BF_4^-$, $PF_6^-$, $SbF_6^-$), nitrate, and fluorosulfate.

In addition to the anions A, neutral ligands, such as water or solvent molecules or the substrates to be reacted (alcohols, amines), can supplement the coordination sphere.

In Formula schemes VII, VIII and IX, the substituents also have the following meanings:

$R^1$ represents hydrogen, an alkyl radical having from 1 to 20 carbon atoms, an aryl or heteroaryl group, an OR group in which R represents hydrogen or an alkyl group having from 1 to 20 carbon atoms, or NRR' in which R and R' each represent hydrogen or each represent an aryl or alkyl group having from 1 to 20 carbon atoms, or R and R' together form a ring system having a nitrogen atom as heteroatom.

$R^2$ represents hydrogen, an alkyl group having from 1 to 20 carbon atoms, an aryl group or heteroaryl group which is linked via one or two C—C bonds fused to the salicylate structural unit, a keto group —COR or —COOR, —COOH, fluorine, chlorine, bromine, iodine, OH, OR or NRR', in which R and R' can have the meanings given above, and $R^2$ can substitute the aromatic ring from 1 to 4 times.

$R^3$ represents hydrogen, an alkyl group having from 1 to 20 carbon atoms, an aryl or heteroaryl group, OH, OR or NRR', in which R and R' have the meanings given above.

By means of these catalysts it is possible, without the addition of halogen-containing promoters in the oxidative carbonylation of an amine in the presence of a hydroxyl-group-containing compound to produce the corresponding urethanes, to achieve conversions and selectivities of up to over 95% (i.e., yields of up to over 90%), based on the amine used. The oxidative carbonylation process of the present invention is represented by either of the following general reaction equations, in which R—$NH_2$ represents a monofunctional amine or an amino group equivalent of a di- or polyamino compound and R'OH represents a monofunctional hydroxyl compound or a hydroxyl group equivalent of a di- or poly-hydroxy compound.

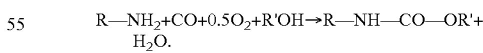

$$R—NH_2+CO+0.5O_2+R'OH \rightarrow R—NH—CO—OR'+H_2O.$$

R is a primary or secondary aliphatic or aromatic radical. R and R' can also be identical.

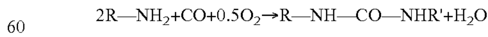

$$2R—NH_2+CO+0.5O_2 \rightarrow R—NH—CO—NHR'+H_2O$$

R is a primary or secondary aliphatic or aromatic radical. R and R' can also be identical.

Within the scope of this invention, aliphatic radicals are to be understood as being both linear and branched and also cyclic aliphatic radicals.

The process of the present invention is carried out in the absence of halogen-containing promoters. This process thereby differs from known processes (e.g., U.S. Pat. No. 5,194,660) in which from 0.05 to 10 wt. % (based on the weighed amount of all components) of the necessary promoter is used. In the above-mentioned literature, halogen-containing promoters are ionic halides of the alkali metals (e.g., sodium chloride, potassium chloride, sodium bromide, sodium iodide), of the alkaline earth metals (e.g., calcium chloride, strontium bromide, barium iodide) as well as so-called onium ions of the general formula $(R_1R_2R_3R_4E)X$ in which $R_1$ to $R_4$ each represents hydrogen, aliphatic or aromatic radicals of any substitution, E represents the elements nitrogen, phosphorus, arsenic, antimony, sulfur, selenium, tellurium, and X represents any of the halides fluorine, chlorine, bromine and iodine.

An advantage of working without halogen-containing promoters is that it is not necessary to pre-purify the starting materials, and the separation, recovery and/or recycling of the mentioned halogen-containing promoters is avoided.

Suitable amines (amino compounds) for the process of the present invention for the preparation of urethanes and/or ureas are primary and secondary amines. Primary amines are preferred because, for example, the urethanes obtained therefrom can be converted into the corresponding isocyanates in an additional process step, for example, by thermolysis with cleavage of the hydroxyl compound. Examples of suitable primary amines are: aliphatic mono-, di- and/or poly-amines, mixed aliphatic-cycloaliphatic mono-, di- and/or poly-amines, cycloaliphatic mono-, di- and/or poly-amines, aromatic mono-, di- and/or poly-amines, araliphatic mono-, di- and/or poly-amines or mixtures comprising two or more of the above primary amines.

Specific but non-limiting examples of suitable primary monoamines are aniline, anilines mono- or poly-substituted on the aromatic ring, such as the isomeric toluidines or halogenated anilines, benzylamine, 2-phenylethylamine, 1-phenylethylamine, cyclohexylamine, substituted cyclohexylamines, methylamine, ethylamine, the isomeric propyl-, butyl-, pentyl-amines and their higher homologues.

Specific but non-limiting examples of suitable primary diamines are o-phenylenediamine, m-phenylenediamine, p-phenylenediamine, phenylenediamines mono- or poly-substituted on the aromatic ring, such as tetramethylphenylenediamine, the isomeric diaminotoluenes, such as 2,4-diaminotoluene and 2,6-diaminotoluene, the isomeric diaminodiphenylmethanes, such as 4,4'-diaminodiphenylmethane, 2,4'-diaminodiphenylmethane or 2,2'-diaminodiphenylmethane, naphthalenediamines, such as 1,4-naphthalenediamine, 1,5-naphthalenediamine or 1,8-naphthalenediamine, o-xylylenediamine, m-xylylenediamine, p-xylylenediamine, the isomeric diaminocyclohexanes, diaminocyclohexanes substituted on the cycloaliphatic ring, isophoronediamine, ethylenediamine, 1,2-diaminopropane, $\alpha,\omega$-diaminoalkanes, such as 1,3-diaminopropane, and also higher homologues, such as 1,6-hexamethylenediamine, and substituted $\alpha,\omega$-diaminoalkanes.

Specific but non-limiting examples of suitable primary polyamines are mixtures, obtained by condensation of aniline with formaldehyde, of the isomeric diaminodiphenylmethanes with their higher homologues and their isomers of the polyfunctional amines of the diphenylmethane group.

Specific but non-limiting examples of organic compounds containing one or more hydroxyl groups are alcohols, in particular the aliphatic alcohols such as methanol, ethanol and the higher homologous alkanols and their isomers, such as n-propanol, iso-propanol, n-butanol, iso-butanol, sec-butanol, etc., mono- or poly-halosubstituted derivatives of the above alcohols, such as trifluoroethanol or hexafluoroisopropanol, cycloaliphatic alcohols such as cyclopentanol or cyclohexanol, benzyl alcohol, phenol or substituted phenols (e.g., cresols).

The metal complex catalyst required for the reaction is preferably used in a concentration of from 0.01 to 10 mol %, preferably from 0.05 to 5 mol %, most preferably from 0.1 to 3 mol %, per mole of amino groups.

In the oxidative carbonylation of an amine in the presence of a hydroxyl-group-containing compound to give the corresponding urethanes, the hydroxyl-group-containing compound is used in an at least stoichiometric amount, based on the amount of amino groups. An excess of the hydroxyl-group-containing compound, based on the amount of amino groups, is preferably used. Preference is given to the use of from 2 to 100 mol of hydroxyl groups per mole of amino groups and most preferably, from 5 to 50 mol of hydroxyl groups are used per mol of amino groups.

In general, the hydroxyl-group-containing compound, in particular when it is used in excess, serves as solvent. However, it is also possible to use an additional solvent. Suitable additional solvents include any of the known solvents that are inert under the reaction conditions. Examples of suitable solvents, which are not to be regarded as limiting, however, are aliphatic and aromatic hydrocarbons and their halogenated derivatives, such as benzene, toluene, the isomeric xylenes, ethylbenzene, chlorobenzene, the isomeric dichlorobenzenes, ethers, esters, etc.

In another embodiment of the present invention, water-containing solvents are used.

In a further embodiment of the present invention, it is preferred to use solvents that have not been halogenated. As already described above, solvents are either the hydroxyl-group-containing compound, in particular when it is used in excess, or an additional solvent. This has the advantage that the process can be carried out substantially halogen-free, which is advantageous from an ecological point of view and is economically expedient because the handling of additional, in particular chlorinated, compounds is thereby avoided.

The carbonylation reaction is carried out preferably above 0° C., more preferably in the temperature range from 20° C. to 250° C., most preferably at from 80 to 220° C.

The amount of carbon monoxide used is at least the stoichiometric amount required for the reaction, based on the amino groups that are present. A 10-fold, more preferably a 15-fold, excess of carbon monoxide is preferably used. The absolute partial pressure of the carbon monoxide used, at room temperature, is from 1 to 150 bar, most preferably from 10 to 100 bar.

The amount of oxygen used is such at least the stoichiometric amount required for the reaction, based on the amino groups that are present. A 1.2-fold, more preferably a 1.6-fold, excess of oxygen is preferably used. The absolute partial pressure of the oxygen used, at room temperature, is from 1 to 20 bar, most preferably from 1 to 10 bar. It is particularly advantageous to work outside the explosion limits of $CO/O_2$.

The oxygen can be provided either in the form of pure oxygen or in admixture with gases that are inert under the reaction conditions, such as nitrogen, $CO_2$, noble gases, etc. It is possible to use either one of those inert gases or a mixture of two or more inert gases. Use of either pure oxygen or air is preferred.

Under the reaction conditions (i.e., above room temperature), the autogenic pressure of the reaction mixture is established, which is above atmospheric pressure.

In the process of the present invention, the corresponding urethanes are formed by oxidative carbonylation of an amine in the presence of a hydroxyl-group-containing compound. In the course of the reaction, the ureas based on the amine can optionally also be formed as intermediates and/or secondary products. In the further conduct of the reaction, the ureas can react further, partially or completely, with the hydroxyl-group-containing compound by alcoholysis to form the corresponding urethane(s).

In principle, however, the ureas can also be prepared by oxidative carbonylation of amino compounds in the presence of carbon monoxide and oxygen and in the absence of organic, hydroxyl-group-carrying compounds. In this process, the carbonylation is carried out in the presence of metal complex catalysts which contain neutral bidentate N-chelate ligands of the (N~N) type, two monoanionic N,O-chelate ligands of the general type $(N\sim O)^{-}$ or tetradentate dianionic chelate ligands $(O\sim N\sim N\sim O)^{2-}$.

For working up the reaction mixture and for isolating the product, the processes known to the person skilled in the art, or any desired combinations of the known processes, can be used. Examples of suitable processes include distillation, crystallization, filtration, extraction, separation by means of membrane processes, etc. Starting materials, intermediates, solvents and/or catalysts can be recovered and fed back into the process again at a suitable point.

The process of the present invention can be carried out batchwise, semi-continuously or continuously.

The resulting urethane can preferably be converted into the corresponding isocyanate in a further process stage, for example, by thermal or chemical means. The thermolysis can be carried out with or without catalysis, and without a solvent or in the presence of a suitable solvent. The hydroxyl-group-containing compound can thereby be recovered and used in the urethane synthesis again. By closing the circuit of the hydroxyl-group-containing compound, the process as a whole can be made economically more attractive because it is necessary to compensate for only those losses of hydroxyl-group-containing compound due to irreversible secondary reactions.

The present invention therefore relates also to a process for the preparation of isocyanates, in which urethanes are prepared by oxidative carbonylation of the corresponding amines in the presence of the required catalyst(s) and then the urethane is converted into the corresponding isocyanate by thermal means.

The carbonylation and the thermolysis are preferably carried out in one process step.

The process according to the invention is explained in detail by the following examples.

EXAMPLES

Example 1

Reported as Entry 11 in Table 1

The oxidative carbonylation reaction was carried out in a 100 $cm^3$ stainless steel autoclave having a polytetrafluoroethylene beaker as an insert. 0.0845 g (0.22 mmol) of N,N'-bis (salicylidene)-1,2-phenylene diaminocobalt(II), 1.023 g (11.0 mmol) of aniline and 10.692 g (297.2 mmol) of methanol were mixed in the autoclave. The autoclave was filled at room temperature (about 25° C.) with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 100% and the methyl-N-phenylcarbamate yield was 95%.

Example 2

Reported as Entry 10 in Table 1

The reaction described in Example 1 was repeated in a stainless steel autoclave having a polytetrafluoroethylene beaker of 100 $cm^3$ capacity. 0.0714 g (0.22 mmol) of N,N'-bis(salicylidene)-ethylene diaminocobalt(II), 1.023 g (11.0 mmol) of aniline, 10.692 g (297.2 mmol) of methanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 100% and the methyl-N-phenylcarbamate yield was 69%.

COMPARISON EXAMPLES

Entry 1 reported in Table 1 reflects the yield obtained for a product prepared under exactly the same conditions with the same materials used in Example 1 with the exception that no catalyst was used.

Entry 2 reported in Table 1 reflects the yield obtained for a product prepared under exactly the same conditions with the same materials used in Example 2, with the exception that cobalt acetate tetrahydrate was the catalyst used.

Each of Entries 3-8 reported in Table 1 reflects the yield obtained for a product prepared under exactly the same conditions with the same materials that were used in Example 1, with the exception that the catalyst employed was the catalyst recited in Table 1 rather than $Co^{II}$(Salophen).

TABLE 1

| | | Aniline | Methyl-N-phenylcarbamate | |
|---|---|---|---|---|
| Entry | Catalyst | Conversion [%] | Selectivity [%] | Yield [%] |
| 1 | — | 12.0 | — | — |
| 2 | $Co^{II}(OAc)_2$ | 65.9 | 44.9 | 29.6 |
| 3 | $Co^{II}(OAc)_2$ + 1 eq. 1,10-Phen | 90.8 | 62.1 | 56.4 |
| 4 | $[Co^{II}(Quin)_2(H_2O)_2]$ | 71.0 | 63.7 | 45.2 |
| 5 | $[Co^{II}(Pico)_2(H_2O)_2]$ | 43.6 | 46.6 | 20.3 |
| 6 | $[Co^{II}(GHA)]$ | 67.2 | 56.1 | 37.7 |
| 7 | $[Co^{II}(Bpphen)]$ | 70.1 | 98.8 | 69.3 |
| 8 | $[Co^{II}(BABHQ)]$ | 100 | 70.6 | 70.6 |
| 9 | $[Co^{II}(BAMHQ)]$ | 100 | 83.3 | 83.3 |

TABLE 1-continued

| | | | | |
|---|---|---|---|---|
| 10 | [$Co^{II}$(Salen)] | 95.2 | 72.7 | 69.2 |
| 11 | [$Co^{II}$(Salophen)] | 100 | 95.0 | 95.0 |

Table 1, reaction conditions: 165° C., 4 bar $O_2$, 36 bar CO, reaction time 3 h, $n_{cat}/n_{aniline}$ = 1/50, $n_{MeOH}/n_{aniline}$ = 27/1.

Percentages are based on aniline used.

Abbreviations used in Table 1:

1,10-Phen = 1,10-phenanthroline;

Bpphen = 2,9-bis(2-hydroxyphenyl)-1,10-phenanthroline;

BAMHQ = bis-aminomethyl-bis(8-hydroxyquinoline);

BABHQ = bis-aminobutyl-bis(8-hydroxyquinoline);

Salophen = N,N'-bis(salicylidene)-1,2-phenylenediamine;

Salen = N,N'-bis(salicylidene)-ethylenediamine;

GHA = glyoxal-bis(2-hydroxyanil);

Quin = quinoline;

Pico = picoline;

OAc = acetate, $n_{cat}/n_{aniline}$ = molar ratio catalyst to aniline, $n_{MeOH}/n_{aniline}$ = molar ratio methanol to aniline.

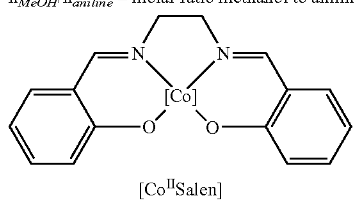

[$Co^{II}$Salen]

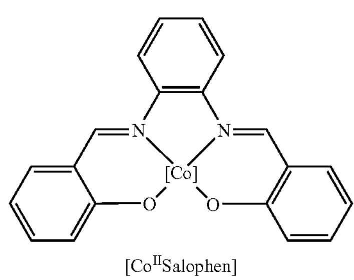

[$Co^{II}$Salophen]

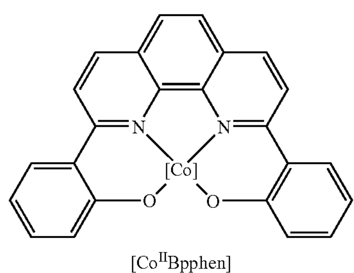

[$Co^{II}$Bpphen]

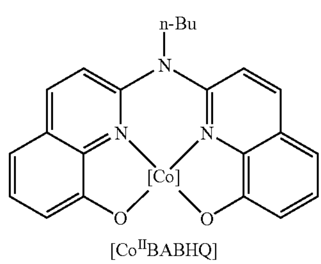

[$Co^{II}$BABHQ]

TABLE 1-continued

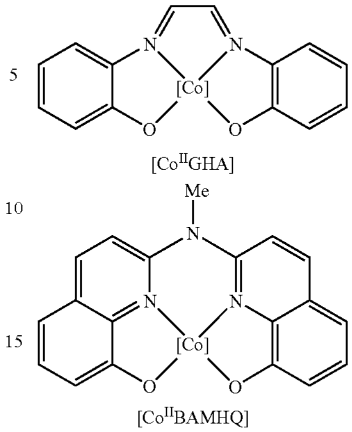

[$Co^{II}$GHA]

[$Co^{II}$BAMHQ]

Example 3

Reported as Entry 9 in Table 1

The reaction described in Example 1 was again carried out in a stainless steel autoclave having a polytetrafluoroethylene beaker of 100 $cm^3$ capacity. 0.0828 g (0.22 mmol) of bis-aminomethyl-bis(8-hydroxyquinoline) cobalt(II), 1.023 g (11.0 mmol) of aniline, and 10.692 g (297.2 mmol) of methanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 100% and the methyl-N-phenylcarbamate yield was 83%.

Each of Entries 1-9 reported in Table 2 reflects the yield obtained for a product prepared under exactly the same conditions and with the same materials that were used in Example 1, with the exception that the catalyst employed was the catalyst recited in Table 2.

TABLE 2

| | | Aniline | Methyl-N-phenylcarbamate | |
|---|---|---|---|---|
| Entry | Catalyst | Conversion [%] | Selectivity [%] | Yield [%] |
| 1 | [$Co^{II}$(Salpryln)] | 44.5 | 30.6 | 13.6 |
| 2 | [$Co^{II}$(Salen)] | 53.6 | 53.2 | 28.5 |
| 3 | [$Co^{II}$(Salophen)] | 67.8 | 72.1 | 48.9 |
| 4 | [$Co^{II}$(Salben)] | 24.2 | 33.5 | 8.1 |
| 5 | [$Co^{II}$(Naphthalben)] | 68.5 | 61.8 | 42.3 |
| 6 | [$Co^{II}$(Naphthalophen)] | 55.8 | 74.2 | 41.4 |
| 7 | [$Co^{II}$(Cyclosalen)] | 54.5 | 59.8 | 32.6 |

TABLE 2-continued

| | | | | |
|---|---|---|---|---|
| 8 | [$Co^{II}$($\alpha$-$CH_3$-Salen)] | 77.1 | 57.1 | 44.0 |
| 9 | [$Co^{II}$($\alpha$-Ph-Salen)] | 64.4 | 55.1 | 35.5 |

Table 2, reaction conditions: 165° C., 4 bar $O_2$, 36 bar CO, reaction time = 3 h,
$n_{cat}/n_{aniline}$ = 1/200, $n_{MeOH}/n_{aniline}$ = 27/1.
Percentages are based on aniline used.
Salophen = N,N'-bis(salicylidene)-1,2-phenylenediamine;
Salen = N,N'-bis(salicylidene)-ethylenediamine;
Salpryin = bis(salicylideneiminato-3-propyl)methyl-amine;
Salben = N,N'-bis(salicylidene)-[2,2'-binaphthalene]-1,1'-diamine;
Naphthalben = N,N'-3,3-bis(2-naphthalenol)-ethylenediamine;
Naphthalophen = N,N'-3,3-bis(2-naphthalenol)-1,2-phenylenediamine;
Cyclosalen = N,N'-bis(salicylidene)-1,2-cyclohexylenediamine;
$\alpha$-$CH_3$-Salen = bis(2-hydroxyacetophenone)ethylenediamine;
$\alpha$-Ph-Salen = bis(2-hydroxybenzophenone) ethylenediamine, $n_{cat}/n_{aniline}$ = molar ratio catalyst to aniline,
$n_{MeOH}/n_{aniline}$ = molar ratio methanol to aniline.

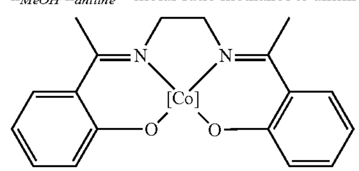

[$Co^{II}$alpha-$CH_3$-Salen]

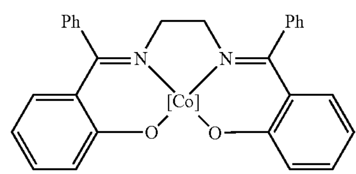

[$Co^{II}$alpha-Ph-Salen]

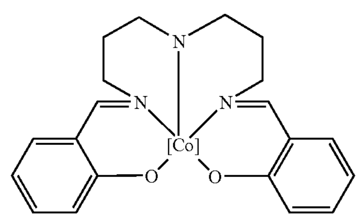

[$Co^{II}$Salpryln]

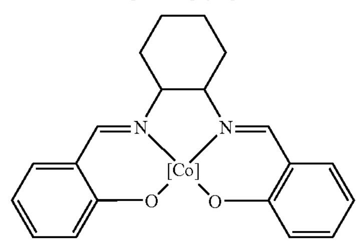

[$Co^{II}$Cyclosalen]

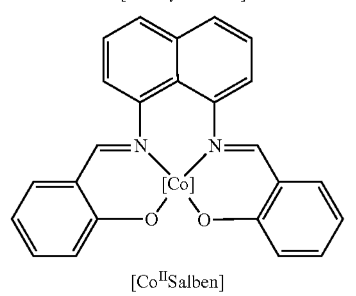

[$Co^{II}$Salben]

TABLE 2-continued

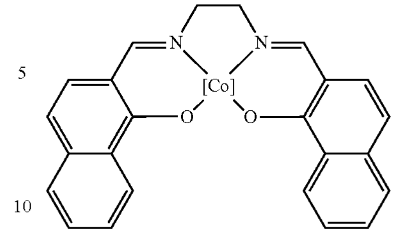

[$Co^{II}$Nalpthalben]

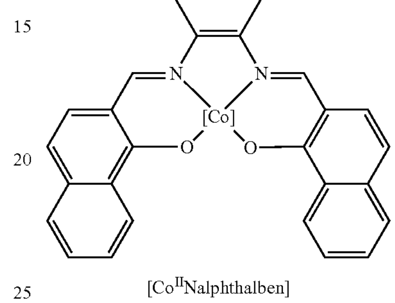

[$Co^{II}$Nalphthalben]

Each of Entries 1-8 reported in Table 3 reflects the yield obtained for a product prepared under exactly the same conditions and with the same materials that were used in Example 1, with the exception that the catalyst employed was the catalyst recited in Table 3 rather than $Co^{II}$(Salophen).

TABLE 3

| | | Aniline | Methyl-N-phenylcarbamate | |
|---|---|---|---|---|
| Entry | Catalyst | Conversion [%] | Selectivity [%] | Yield [%] |
| 1 | [$Co^{II}$(SalenCl$_2$)] | 84.4 | 79.7 | 67.3 |
| 2 | [$Co^{II}$(SalenBr$_2$)] | 49.1 | 60.5 | 29.7 |
| 3 | [$Co^{II}$(SalenMe$_2$)] | 70.7 | 79.4 | 56.1 |
| 4 | [$Co^{II}$(SalenOMe$_2$)] | 31.0 | 71.0 | 22.0 |
| 5 | [$Co^{II}$(SalophenCl$_2$)] | 58.5 | 61.8 | 36.1 |
| 6 | [$Co^{II}$(SalalophenBr$_2$)] | 59.2 | 65.7 | 38.9 |
| 7 | [$Co^{II}$(SalophenMe$_2$)] | 74.2 | 71.3 | 52.9 |
| 8 | [$Co^{II}$(SalophenOMe$_2$)] | 61.6 | 88.0 | 54.2 |

Table 3, reaction conditions: 165° C., 4 bar $O_2$, 36 bar CO, reaction time = 3 h, $n_{cat}/n_{aniline}$ = 1/200, $n_{MeOH}/n_{aniline}$ = 27/1.
Percentages are based on aniline used.
SalenCl$_2$ = N,N'-bis(5-chlorosalicylidene)ethylenediamine;
SalenBr$_2$ = N,N'-bis(5-bromosalicylidene)ethylenediamine;
SalenMe$_2$ = N,N'-bis(5-methylsalicylidene)ethylenediamine;
SalenOMe$_2$ = N,N'-bis(5-methoxysalicylidene)ethylenediamine;
SalophenCl$_2$ = N,N'-bis(5-chlorosalicylidene)-1,2-phenylenediamine;
SalophenBr$_2$ = N,N'-bis(5-bromosalicylidene)-1,2-phenylenediamine;
SalophenMe$_2$ = N,N'-bis(5-methylsalicylidene)-1,2-phenylenediamine;
SalophenOMe$_2$ = N,N'-bis(5-methoxysalicylidene)-1,2-phenylenediamine;
$n_{cat}/n_{aniline}$ = molar ratio catalyst to aniline,
$n_{MeOH}/n_{aniline}$ = molar ratio methanol to aniline.

Example 4

Recorded as Entry 1 Table 4

The process described in Example 1 was repeated in a stainless steel autoclave having a polytetrafluoroethylene beaker of 100 cm$^3$ capacity. 0.0714 g (0.22 mmol) of N,N'-bis(salicylidene)-ethylene diaminocobalt(II), 1.023 g (11.0 mmol) of aniline, 22.013 g (297.2 mmol) of n-butanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 89% and the n-butyl-N-phenylcarbamate yield was 60%.

Each of Entries 2-4 reported in Table 4 reflects the yield obtained for a product prepared under exactly the same conditions and with the same materials that were used in Example 4, with the exception that a different catalyst was employed.

TABLE 4

| | | Aniline | n-Butyl-N-phenylcarbamate | |
|---|---|---|---|---|
| Entry | Catalyst | Conversion [%] | Selectivity [%] | Yield [%] |
| 1 | [$Co^{II}$(Salen)] | 89.0 | 67.8 | 60.3 |
| 2 | [$Co^{II}$(Salophen)] | 80.7 | 64.2 | 51.8 |
| 3 | [$Co^{II}$(α-$CH_3$-Salen)] | 76.9 | 69.8 | 53.7 |
| 4 | [$Co^{II}$(α-Ph-Salen)] | 76.7 | 54.1 | 41.5 |

Table 4, reaction conditions: 165° C., 4 bar $O_2$, 36 bar CO, reaction time = 3 h, $n_{cat}/n_{aniline}$ = 1/50, $n_{n\text{-}BuOH}/n_{aniline}$ = 27/1.
Percentages are based on aniline used.
Salophen = N,N'-bis(salicylidene)-1,2-phenylenediamine;
Salen = N,N'-bis(salicylidene)-ethylenediamine;
α-$CH_3$-Salen = bis(2-hydroxyacetophenone)ethylenediamine;
α-Ph-Salen = bis(2-hydroxybenzophenone)ethylenediamine,
$n_{cat}/n_{aniline}$ = molar ratio catalyst to aniline,
$n_{n\text{-}BuOH}/n_{aniline}$ = molar ratio n-butanol to aniline.

Example 5

Reported as Entry 3 in Table 5

The process described in Example 1 was repeated in a stainless steel autoclave having a polytetrafluoroethylene beaker of 100 cm$^3$ capacity. 0.0828 g (0.22 mmol) of bis-aminomethyl-bis(8-hydroxyquinoline) cobalt(II), 1.023 g (11.0 mmol) of aniline, 29.720 g (297.2 mmol) of 2,2,2-trifluoroethanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 99% and the 2,2,2-trifluoroethyl-N-phenylcarbamate yield was 96%.

Each of Entries 1, 2 and 4 reported in Table 5 reflects the yield obtained for a product prepared under exactly the same conditions and with the same materials that were used in Example 5, with the exception that a different catalyst was employed.

TABLE 5

| | | Aniline | 2,2,2-Trifluoroethyl-N-phenylcarbamate | |
|---|---|---|---|---|
| Entry | Catalyst | Conversion [%] | Selectivity [%] | Yield [%] |
| 1 | [$Co^{II}$(Salen)] | 93.2 | 73.1 | 68.1 |
| 2 | [$Co^{II}$(Salophen)] | 97.6 | 92.7 | 90.5 |
| 3 | [$Co^{II}$(BAMHQ)] | 98.5 | 97.0 | 95.5 |
| 4 | [$Co^{II}$(Bpphen)] | 87.6 | 47.6 | 41.7 |

Table 5, reaction conditions: 165° C., 4 bar $O_2$, 36 bar CO, reaction time = 3 h, $n_{cat}/n_{aniline}$ = 1/50, $n_{CF3CH2OH}/n_{aniline}$ = 27/1.
Percentages are based on aniline used.
Salophen = N,N'-bis(salicylidene)-1,2-phenylenediamine;
Salen = N,N'-bis(salicylidene)-ethylenediamine;
Bpphen = 2,9-bis(2-hydroxyphenyl)-1,10-phenanthroline;
BAMHQ = bis-aminomethyl-bis(8-hydroxyquinoline);
$n_{cat}/n_{aniline}$ = molar ratio catalyst to aniline,
$n_{CF3CH2OH}/n_{aniline}$ = molar ratio $CF_3CH_2OH$ to aniline.

Example 6

Reported as Entry 2 in Table 6

The process described in Example 1 was repeated in a 100 cm$^3$ stainless steel autoclave having a polytetrafluoroethylene beaker as insert. 0.0845 g (0.22 mmol) of N,N'-bis(salicylidene)-1,2-phenylene diaminocobalt(II), 1.023 g (11.0 mmol) of aniline, 13.692 g (297.2 mmol) of ethanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 96% and the ethyl-N-phenylcarbamate yield was 74%.

Entry 1 reported in Table 6 reflects the yield obtained for a product prepared under exactly the same conditions and with the same materials that were used in Example 6, with the exception that a different catalyst was employed.

TABLE 6

| | | Aniline | Ehtyl-N-phenylcarbamate | |
|---|---|---|---|---|
| Entry | Catalyst | Conversion [%] | Selectivity [%] | Yield [%] |
| 1 | [$Co^{II}$(Salen)] | 90.9 | 70.8 | 64.4 |
| 2 | [$Co^{II}$(Salophen)] | 96.1 | 77.3 | 74.3 |

Table 6, reaction conditions: 165° C., 4 bar $O_2$, 36 bar CO, reaction time = 3 h, $n_{cat}/n_{aniline}$ = 1/50, $n_{EtOH}/n_{aniline}$ = 27/1.
Percentages are based on aniline used.
Salophen = N,N'-bis(salicylidene)-1,2-phenylenediamine;
Salen = N,N'-bis(salicylidene)-ethylenediamine;
$n_{cat}/n_{aniline}$ = molar ratio catalyst to aniline,
$n_{EtOH}/n_{aniline}$ = molar ratio ethanol to aniline.

Example 7

Reported as Entry 2 in Table 7

The process described in Example 1 was repeated in a stainless steel autoclave having a polytetrafluoroethylene beaker of 100 cm$^3$ capacity. 0.0845 g (0.22 mmol) of N,N'- bis(salicylidene)-1,2-phenylene diaminocobalt(II), 0.805 g (11.0 mmol) of t-butylamine, 10.692 g (297.2 mmol) of methanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The t-butylamine conversion was 95% and the methyl-N-tert-butylcarbamate yield was 87%.

Entry 1 reported in Table 7 reflects the yield obtained for a product prepared under exactly the same conditions and with the same materials that were used in Example 7, with the exception that a different catalyst was employed.

TABLE 7

| | | t-Butylamine | Methyl-N-tert-butyl-carbamate | |
|---|---|---|---|---|
| Entry | Catalyst | Conversion [%] | Selectivity [%] | Yield [%] |
| 1 | [$Co^{II}$(Salen)] | 95 | 93 | 88 |
| 2 | [$Co^{II}$(Salophen)] | 91 | 96 | 87 |
| 3 | [$Co^{II}$(BABHQ)] | 100 | 96 | 96 |
| 4 | [$Co^{II}$(BAMHQ)] | 100 | 91 | 91 |
| 5 | [$Co^{II}$(Bpphen)] | 100 | 71 | 71 |

Table 7, reaction conditions: 165° C., 4 bar $O_2$, 36 bar CO, reaction time = 3 h, $n_{cat}/n_{t\text{-}butylamine}$ = 1/50, $n_{MeOH}/n_{t\text{-}butylamine}$ = 27/1.
Percentages are based on t-butylamine used.
Salophen = N,N'-bis(salicylidene)-1,2-phenylenediamine;
Salen = N,N'-bis(salicylidene)-ethylenediamine;
BABHQ = Bis-aminobutyl-bis(8-hydroxyquinolin);
BAMHQ = Bis-aminomethyl-bis(8-hydroxyquinolin);
Bpphen = 2,9-bis(2-hydroxyphenyl)-1,10-phenanthrolin;
$n_{cat}/n_{t\text{-}butylamine}$ = molar ratio catalyst to t-butylamine,
$n_{MeOH}/n_{t\text{-}butylamine}$ = molar ratio methanol to t-butylamine

Example 8

Reported as Entry 2 in Table 8

The process described in Example 1 was repeated in a stainless steel autoclave having a polytetrafluoroethylene beaker of 100 $cm^3$ capacity. 0.0845 g (0.22 mmol) of N,N'-bis(salicylidene)-1,2-phenylene diaminocobalt(II), 0.805 g (11.0 mmol) of n-butylamine, 10.692 g (297.2 mmol) of methanol were mixed in the autoclave. The autoclave was filled at room temperature with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The n-butylamine conversion was 97% and the methyl-N-n-butylcarbamate yield was 45%.

Entry 1 reported in Table 8 reflects the yield obtained for a product prepared under exactly the same conditions and with the same materials that were used in Example 8, with the exception that a different catalyst was employed.

TABLE 8

| | | n-Butylamine | Methyl-n-butylcarbamate | |
|---|---|---|---|---|
| Entry | Catalyst | Conversion [%] | Selectivity [%] | Yield [%] |
| 1 | [$Co^{II}$(Salen)] | 96 | 49 | 47 |
| 2 | [$Co^{II}$(Salophen)] | 97 | 48 | 47 |
| 3 | [$Co^{II}$(BABHQ)] | 94 | 75 | 70 |
| 4 | [$Co^{II}$(BAMHQ)] | 94 | 81 | 76 |
| 5 | [$Co^{II}$(Bpphen)] | 94 | 75 | 70 |

Table 8, reaction conditions: 165° C., 4 bar $O_2$, 36 bar CO, reaction time = 3 h, $n_{cat}/n_{n\text{-}butylamine}$ = 1/50, $n_{MeOH}/n_{n\text{-}butylamine}$ = 27/1.
Percentages are based on n-butylamine used.
Salophen = N,N'-bis(salicylidene)-1,2-phenylenediamine;
Salen = N,N'-bis(salicylidene)-ethylenediamine;
BABHQ = Bis-aminobutyl-bis(8-hydroxyquinolin);
BAMHQ = Bis-aminomethyl-bis(8-hydroxyquinolin);
Bpphen = 2,9-bis(2-hydroxyphenyl)-1,10-phenanthrolin;
$n_{cat}/n_{n\text{-}butylamine}$ = molar ratio catalyst to n-butylamine,
$n_{MeOH}/n_{n\text{-}butylamine}$ = molar ratio methanol to n-butylamine.

Example 9

Reported as Entry 4 in Table 9

The process described in Example 1 was repeated in a 100 $cm^3$ stainless steel autoclave having a polytetrafluoroethylene beaker as insert. 0.0845 g (0.22 mmol) of N,N'-bis(salicylidene)-1,2-phenylene diaminocobalt(II), 1.023 g (11.0 mmol) of aniline and 10 g (108.5 mmol) of toluene were mixed in the autoclave. The autoclave was filled at room temperature (about 25° C.) with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, naphthalene being used as internal standard. The aniline conversion was 79% and the diphenylurea yield was 64%.

Each of Entries 1-3 reported in Table 9 reflects the yield obtained for a product prepared under exactly the same conditions and with the same materials that were used in Example 9, with the exception that a different catalyst was employed.

TABLE 9

| | | Aniline | Diphenylurea | |
|---|---|---|---|---|
| Entry | Catalyst | Conversion [%] | Selectivity [%] | Yield [%] |
| 1 | [$Co^{II}$(Bpphen)] | 93.2 | 74.4 | 69.4 |
| 2 | [$Co^{II}$(BAMHQ)] | 80.2 | 74.4 | 59.7 |
| 3 | [$Co^{II}$(Salen)] | 71.7 | 72.0 | 51.6 |
| 4 | [$Co^{II}$(Salophen)] | 78.6 | 81.3 | 63.9 |

Table 9, reaction conditions: 165° C., 4 bar $O_2$, 36 bar CO, reaction time = 3 h, $n_{cat}/n_{aniline}$ = 1/50, $n_{toluene}/n_{aniline}$ = 10/1.
Percentages are based on aniline used.
Abbreviations:
Bpphen = 2,9-bis(2-hydroxyphenyl)-1,10-phenanthroline;
BAMHQ = bis-aminomethyl-bis(8-hydroxyquinoline);
Salophen = N,N'-bis(salicylidene)-1,2-phenylenediamine;
Salen = N,N'-bis(salicylidene)-ethylenediamine;
$n_{cat}/n_{aniline}$ = molar ratio catalyst to aniline,
$n_{toluene}/n_{aniline}$ = molar ratio toluene to aniline.

Example 10

Reported as Entry 5 in Table 10

The process described in Example 1 was repeated in a 100 $cm^3$ stainless steel autoclave having a polytetrafluoroethylene beaker as insert. 0.055 g (0.22 mmol) of cobalt(II) acetate tetrahydrate, 0.035 g (0.22 mol) of 2,2'-bipyridine, 1.023 g (11.0 mmol) of aniline and 10.692 g (297.2 mmol) of methanol were mixed in the autoclave. The autoclave was filled at room temperature (about 25° C.) with a mixture of 4 bar oxygen gas and 36 bar carbon monoxide gas. When the gas supply to the autoclave had been stopped, the autoclave was inserted into an aluminum heating block, which was heated to 200° C. In the course of 5 minutes, the autoclave reached a reaction temperature of 165° C., which was then kept constant. After a reaction time of 3 hours, the autoclave was cooled with cold water and ice until, after about 5 minutes, it reached room temperature. The reaction mixture was then analyzed qualitatively and quantitatively by gas chromatography, using naphthalene as the internal standard. The aniline conversion was 92% and the methyl-N-phenylcarbamate yield was 68%.

Each of Entries 1-4 and 6-10 reported in Table 10 reflects the yield obtained for a product prepared under exactly the same conditions and with the same materials that were used in Example 10, with the exception that a different catalyst was employed.

TABLE 10

| | | Aniline | Methyl-N-phenylcarbamate | |
|---|---|---|---|---|
| Entry | Catalyst | Conversion [%] | Selectivity [%] | Yield [%] |
| 1 | $Co(OAc)_2 * 4H_2O$ | 63 | 46 | 29 |
| 2 | $Co(OAc)_2 * 4H_2O$ 1 eq. 1,10-Phen | 94 | 55 | 52 |
| 3 | $Co(OAc)_2 * 4H_2O$ 1 eq. 1,10-Phen[a] | 91 | 62 | 56 |
| 4 | $Co(OAc)_2 * 4H_2O$ 2 eq. 1,10-Phen | 14 | 14 | 2 |
| 5 | $Co(OAc)_2 * 4H_2O$ 1 eq. 2,2'-Bipy | 92 | 73 | 68 |
| 6 | $Co(OAc)_2 * 4H_2O$ 1 eq. 6-(2-methoxyphenyl)-2,2'-bipyridine | 75 | 57 | 43 |
| 7 | $Co(Quin)_2$ | 71 | 63 | 45 |
| 8 | $Co(Pico)_2$ | 43 | 47 | 20 |
| 9 | $Co(Salimin)_2$ | 54 | 33 | 18 |

Table 10, reaction conditions: 165° C., 4 bar $O_2$, 36 bar CO, reaction time = 3 h,
$n_{cat}/n_{aniline}$ = 1/50, $n_{MeOH}/n_{aniline}$ = 27/1.
Percentages are based on aniline used.
[a]The complex was synthesized beforehand.
Abbreviations:
Quin = 8-hydroxyquinoline;
Pico = 2-picolinic acid;
Salimin = 2-[(E)-(phenylimino)methyl]phenol;
OAc = acetate
$n_{cat}/n_{aniline}$ = molar ratio catalyst to aniline,
$n_{MeOH}/n_{aniline}$ = molar ratio methanol to aniline.

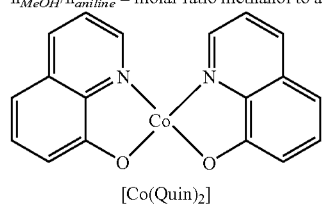

[Co(Quin)₂]

TABLE 10-continued

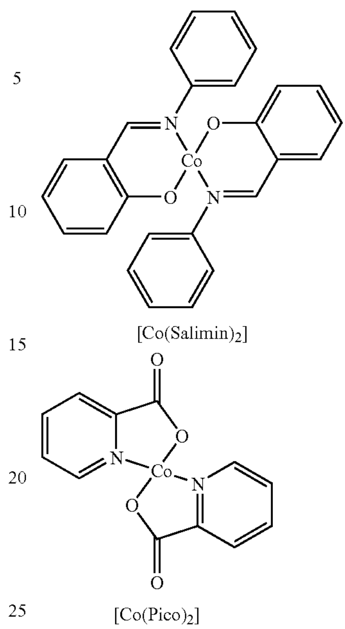

[Co(Salimin)₂]

[Co(Pico)₂]

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An industrial process for the preparation of a urethane by oxidative carbonylation of an amino compound in the presence of carbon monoxide, oxygen and an organic, hydroxyl-group-carrying compound, comprising carrying out the carbonylation in the absence of a halogen-containing promoter and in the presence of a metal complex catalyst comprising a metal complex catalyst of formula scheme V or, wherein:

formula scheme V is:

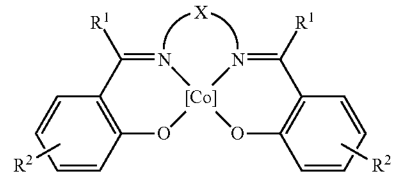

in which:

[Co] represents cobalt in its divalent oxidation state;

$R^1$ represents hydrogen, an alkyl radical having from 1 to 20 carbon atoms, an aryl or heteroaryl group, a OR group in which R represents hydrogen or an alkyl group having from 1 to 20 carbon atoms, or NRR' in which R and R' represent hydrogen or each represent an aryl or alkyl group having from 1 to 20 carbon atoms, or R and R' together can form a ring system containing a nitrogen atom as heteroatom;

$R^2$ represents hydrogen, an alkyl group having from 1 to 20 carbon atoms, an aryl group or heteroaryl group which is linked via one or two C~C bonds fused to the salicylate structural unit, a keto group —COR or —COOR, —COOH, fluorine, chlorine, bromine, iodine, OH, OR or NRR', and $R^2$ can substitute the aromatic ring from 1 to 4 times.; in OR, —COR, and —COOR, R represents hydrogen or an alkyl group having from 1 to 20 carbon atoms, and in NRR', R and R' represent hydrogen or each represent an aryl or alkyl group having from 1 to 20 carbon atoms, or R and R' together can form a ring system containing a nitrogen atom as heteroatom;

X represents any of the aryiene or alkylene structural units, which links the two imino nitrogen atoms with one another; and wherein the carbonylation is carried out in an aliphatic or aromatic alcohol at a temperature of from 80 to 260° C. under an absolute carbon monoxide pressure of from 10 to 100 bar and an absolute oxygen pressure of from 1 to 10 bar, and wherein the carbonylation is carried out in the absence of a halogenated solvent.

2. The industrial process of claim 1, wherein the metal complex catalyst is used in a concentration of from 0.1 to 10 mol %, based on one mole of amino groups.

3. The industrial process of claim 1, wherein the carbonylation is carried out in methanol, ethanol, or n-butanol.

4. The industrial process of claim 1, wherein ureas groups are formed during the carbonylation, wherein these urea groups subsequently react further, partially or completely, with the organic hydroxyl-group-containing compound by alcoholysis to give the corresponding urethanes.

5. The process of claim 1 in which an aliphatic, cycloaliphatic and/or aromatic mono- OF di-amino compound is used.

6. An industrial process for the preparation of isocyanates, comprising:

a) preparing a urethane by carbonylation by the process of claim 1, and b) thermally cleaving the urethane to obtain the isocyanate.

7. The industrial process of claim 6, wherein the carbonylation and the thermal cleavage take place in one process step.

* * * * *